(12) United States Patent
Nichols, Jr.

(10) Patent No.: US 10,314,986 B1
(45) Date of Patent: Jun. 11, 2019

(54) APPARATUSES AND METHODS FOR LOCATING A POSTERIOR PALATAL FORAMEN

(71) Applicant: Russell D. Nichols, Jr., Enterprise, AL (US)

(72) Inventor: Russell D. Nichols, Jr., Enterprise, AL (US)

( * ) Notice: Subject to any disclaimer, the term of this patent is extended or adjusted under 35 U.S.C. 154(b) by 435 days.

(21) Appl. No.: 14/978,825

(22) Filed: Dec. 22, 2015

Related U.S. Application Data

(63) Continuation-in-part of application No. 14/175,648, filed on Feb. 7, 2014, now abandoned.

(60) Provisional application No. 61/762,159, filed on Feb. 7, 2013.

(51) Int. Cl.
*A61M 5/42* (2006.01)

(52) U.S. Cl.
CPC ....... *A61M 5/427* (2013.01); *A61M 2202/048* (2013.01); *A61M 2210/0637* (2013.01)

(58) Field of Classification Search
CPC .......... A61M 5/46; A61M 2210/00637; A61M 2202/048; A61M 5/427; A61M 39/0208; A61M 2039/0238; A61M 5/425; A61M 5/3146
See application file for complete search history.

(56) References Cited

U.S. PATENT DOCUMENTS

| | | | | |
|---|---|---|---|---|
| 2,044,410 A | * | 6/1936 | Thornberry | A61M 5/427 604/116 |
| 4,041,962 A | * | 8/1977 | Johansson | A61C 15/02 132/323 |
| 4,892,520 A | * | 1/1990 | Gilbaugh | A61B 10/0241 604/117 |
| 5,171,225 A | * | 12/1992 | Sterrett | A61M 5/422 604/112 |

* cited by examiner

*Primary Examiner* — Bhisma Mehta
*Assistant Examiner* — Hamza A Darb
(74) *Attorney, Agent, or Firm* — Maynard Cooper & Gale, P.C.; Brian T. Sattizahn (57) ABSTRACT

The present disclosure generally pertains to an apparatus and method for locating the posterior palatal foramen of a human hard palate. The apparatus includes a guide with a curved base, an elongated tapered shaft and a head. The head further includes a channel positioned between two tabs of varying heights leading to a hole. The longer tab has a curved end. The apparatus is attached to a user's finger and slid along the patients gum. The practitioner receives a tactile sensation when the head of the apparatus contacts the groove of the posterior palatal foramen. The tab guides a needle through the hole in the channel to the exact site of the foramen. The apparatus may also be used to apply pressure at an injection site to reduce or eliminate injection pain.

20 Claims, 5 Drawing Sheets

APPARATUSES AND METHODS FOR LOCATING A POSTERIOR PALATAL FORAMEN

CROSS REFERENCE TO RELATED APPLICATION

This application is a continuation-in-part of U.S. patent application Ser. No. 14/175,648, entitled "Apparatuses and Methods for Locating a Posterior Palatal Foramen," and filed on Feb. 7, 2014, which application claims priority to U.S. Patent Application No. 61/762,159, entitled "Apparatuses and Methods for Locating a Posterior Palatal Foramen," and filed on Feb. 7, 2013, both of which applications are incorporated herein by reference.

BACKGROUND

Due to periodontal fibers, the surface of the palate is hard and has little space for the deposit of anesthetic. To anesthetize the gum tissue of several teeth, multiple injections must be dispensed or one injection can be given at the posterior palatal foramen, if it can be located. The posterior palatal foramen transmits the descending palatine vessels and greater palatine nerve. As a result, the posterior palatal foramen is the site typically used to anesthetize patients for root canals or surgical removal of teeth. Typically, the dentist locates the foramen opening at the front root of the second molar. This can be anywhere along the vertical area; however, the opening is usually in the curvature of the area. Locating this opening and then applying an anesthetic to the posterior palatal foramen can be difficult and burdensome.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
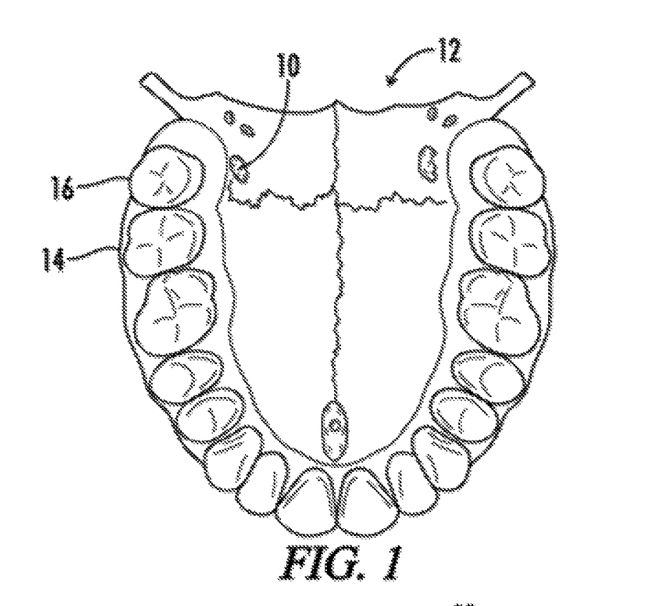
FIG. 1 is depicts a human hard palate.

Referring to FIG. 1, the posterior palatal foramen 10 is a small opening of the hard palate 12 located near the second 14 and third molars 16 in which the palatine vessels and greater palatine nerve (not shown) travel. The depression of the posterior palatal foramen 10 can be felt by a fingertip. The present disclosure generally pertains to apparatuses and methods for assisting users in locating the posterior palatal foramen 10 and applying anesthetic to the posterior palatal foramen 10. In one exemplary embodiment, an apparatus (referred to hereafter as a "foramen guide") extends from a finger and provides feedback to the user to assist the user in finding the posterior palatal foramen. Specifically, the foramen guide provides a tactile sensation that informs the user when a head of the guide reaches the depression of the posterior palatal foramen 10 as the head is being slid across the hard palate gum of a patient. Such a guide also allows pressure to be applied at the area of injection to help reduce discomfort and guide a needle as an anesthetic is being applied.

Figure 2:
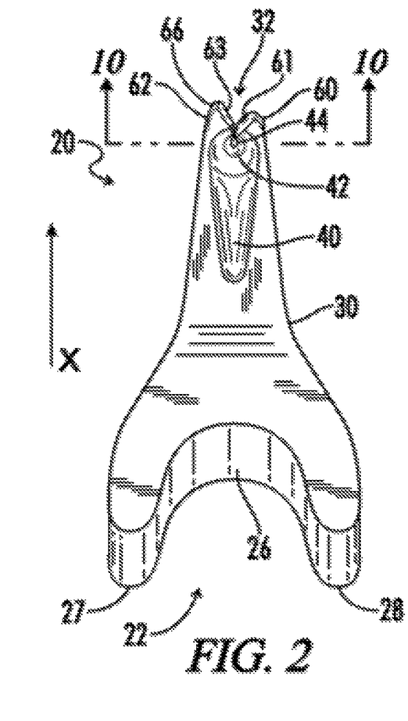
FIG. 2 depicts a top view of an exemplary embodiment of a foramen guide.
Figure 3:
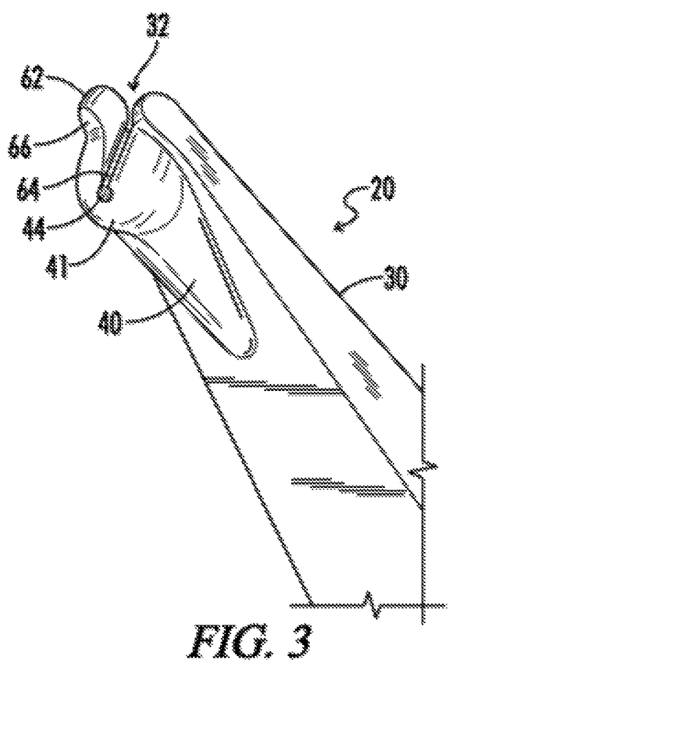
FIG. 3 depicts a bottom view of the foramen guide of FIG. 2.
Figure 4:
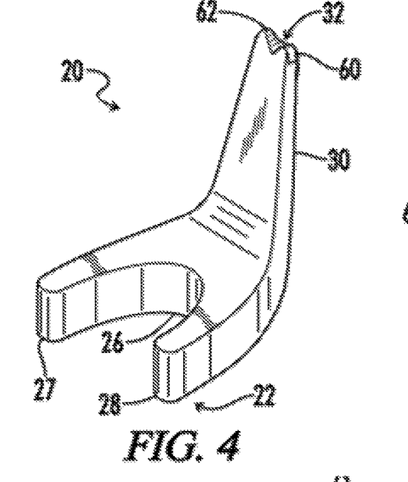
FIG. 4 depicts a side view of the foramen guide of FIG. 2.
Figure 5:
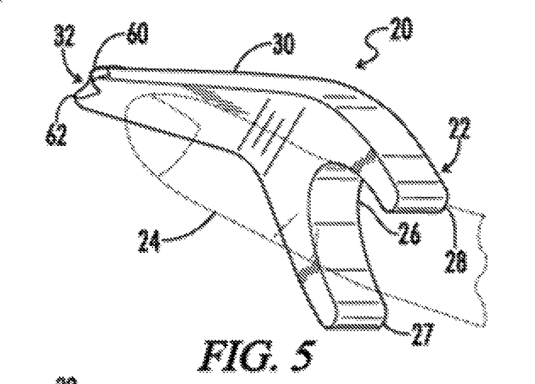
FIG. 5 depicts a side view of the foramen guide of FIG. 2 fitted around a user's finger.

FIGS. 2-8 depict exemplary embodiments of a foramen guide 20. Referring to FIGS. 2 and 5, the guide 20 has a base 22 that is curved in order to wrap around the finger 24 of a user, such as a dentist who is searching for a posterior palatal foramen 10 of a patient for administering an injection of anesthesia through such posterior palatal foramen 10. In one embodiment, base 22 is constructed from a rigid plastic. The base 22 may be constructed from other materials in alternate embodiments, such as a thin flexible metal. In addition to flexibility, the material also exhibits sufficient strength to secure the guide 20 to the user's finger while preventing the guide 20 from slipping during use. The flexible material has a curved orientation forming a groove 26 for receiving the user's finger 24. Specifically, the base 22 has a pair of tongs 27 or 28 separated by groove 26. Referring again to FIG. 5, the elastic nature of the base 22 allows tongs 27 and 28 to deform as the user's finger 24 pushes against the inner walls of tongs 27 and 28 such that the user's finger 24 fits snugly between the tongs 27 or 28. Frictional forces from the snug fit to hold the guide 20 securely in place around the finger 24 during the search for the posterior palatal foramen 10 and the subsequent injection of an anesthetic. The flexible nature of the base 22 allows it expand or contract around the finger 24 to accommodate a wide range of finger sizes. In an additional embodiment, the base 22 forms a loop that completely surrounds the user's finger (not shown). In this configuration, the base 22 may be slid onto the user's finger 24, similar to a jewelry ring. Alternatively, a fastener (e.g., Velcro) may be used to secure the base 22 about the finger. Yet other techniques of securing the base 22 to the finger 24 are possible in other embodiments.

Figure 8:
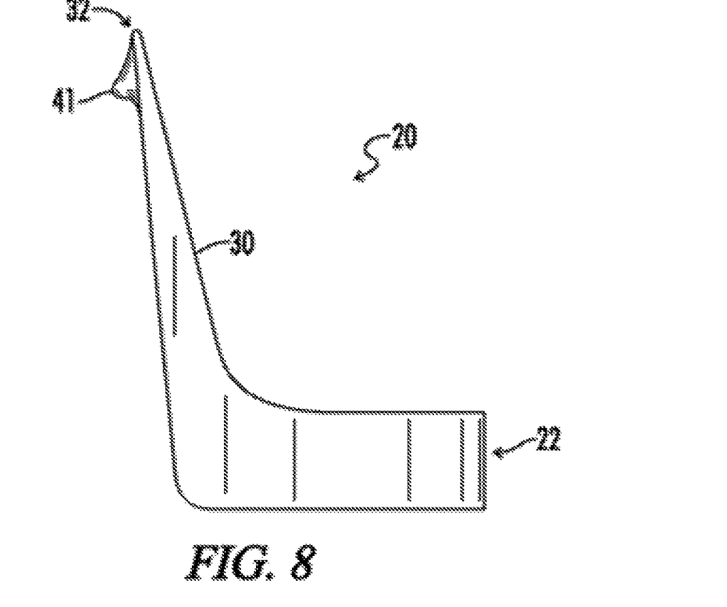
FIG. 8 depicts an additional side view of the foramen guide of FIG. 2.

Turning now to FIGS. 4 and 8, the guide 20 further includes an elongated shaft 30 that extends upward from the curved base 22 to head 32 located on the end of the shaft 30 opposite the base 22. In one embodiment, the width of shaft 30 gradually decreases and tapers as it approaches head 32. The length of the shaft 30 may vary depending on its intended application. For instance, a shorter shaft 30 may be useful for pediatric patients relative to the length of a shaft 30 used for an adult. In the embodiment illustrated in FIG. 8, the shaft 30 extends from the base 22 at an approximate right angle so that the guide 20 forms a bend of approximately 90 degrees. In other embodiments, other angles of the bend are possible, and it is possible for the guide to be implemented without a bend or with multiple bends. Yet other configurations of the shaft 30 and base 22 are also possible. The bend makes it easier for the foramen guide to comfortably fit inside the mouth of a patient while still accommodating a needle or syringe for the injection of an anesthetic. In addition, such bend helps position the shaft 30 so that the user's finger 24 is positioned on the groove 26 where it can easily apply pressure to the shaft 30 and sense movement of the shaft 30, such as when the head 32 moves into the depression formed by the posterior palatal foramen. In one embodiment, the shaft 30 is constructed from the same material utilized in the construction of the base 22. In one embodiment such material is rigid plastic, although other materials, such as a flexible metal, are contemplated in other embodiments.

Figure 9:
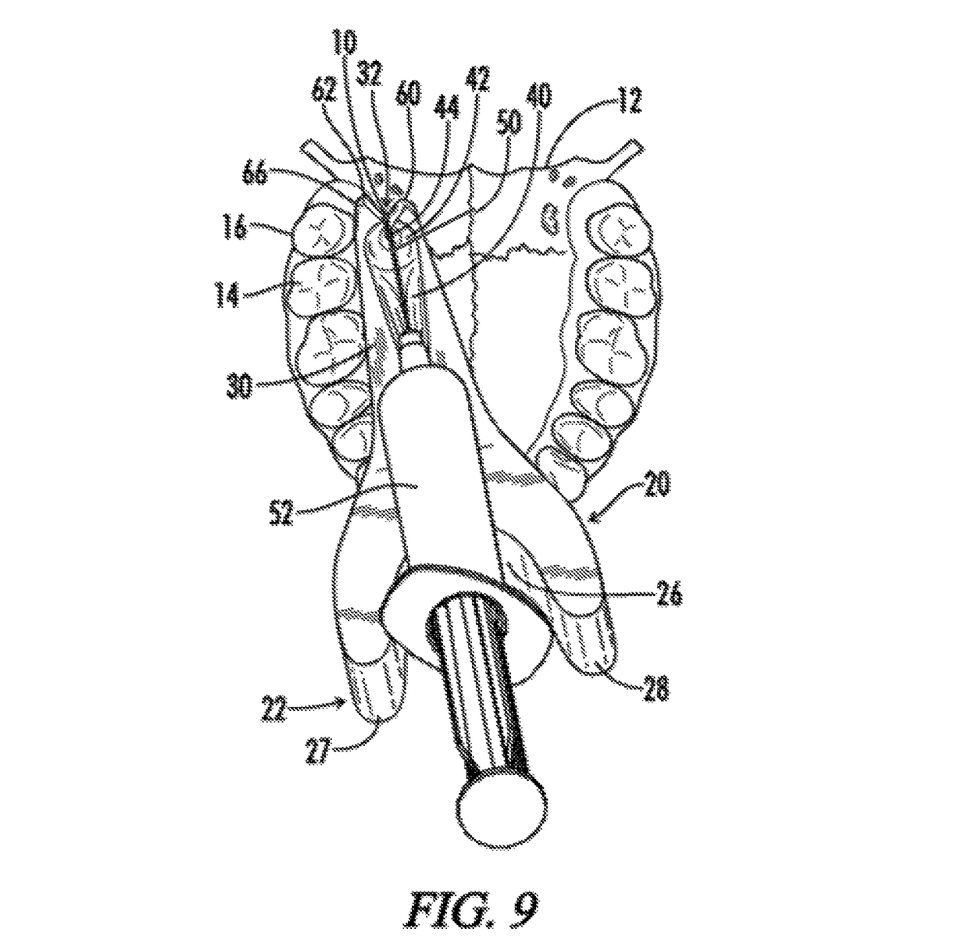
FIG. 9 depicts an illustration of the attachment of the foramen guide of the disclosure to a user's finger.
Figure 10:
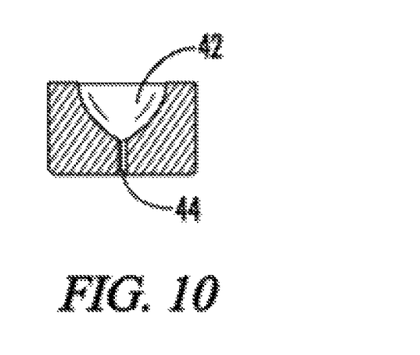
FIG. 10 depicts a cross sectional view of the protrusion and hole, such as is depicted in FIG. 2.
Figure 11:
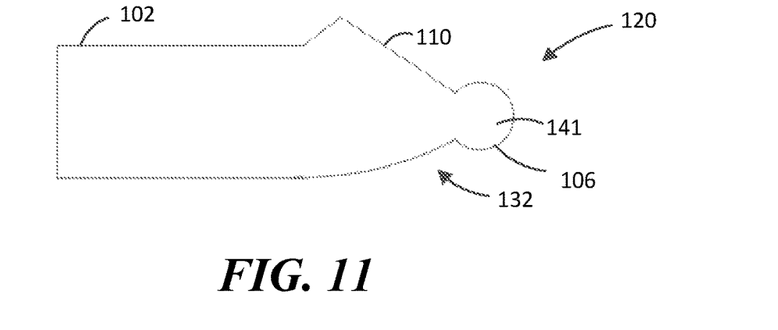
FIG. 11 depicts a side view of another exemplary embodiment of a foramen guide.
Figure 12:
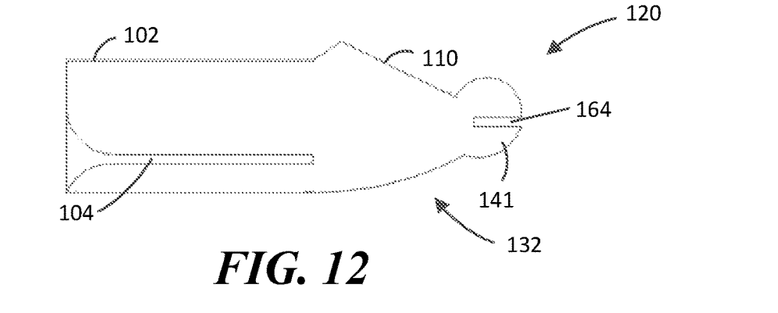
FIG. 12 depicts an alternate side view of the foramen guide of FIG. 11.
Figure 13:
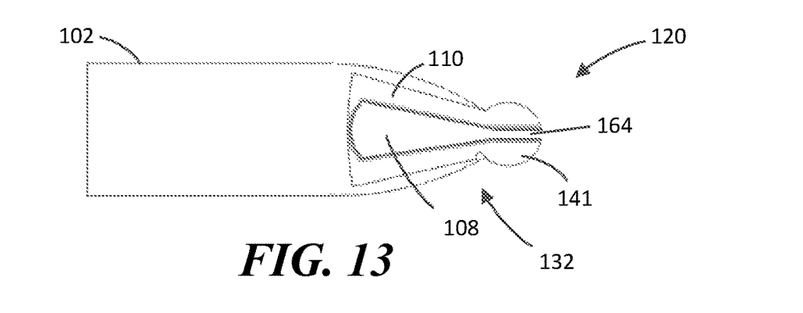
FIG. 13 depicts a top view of the foramen guide of FIG. 11.
Figure 14:
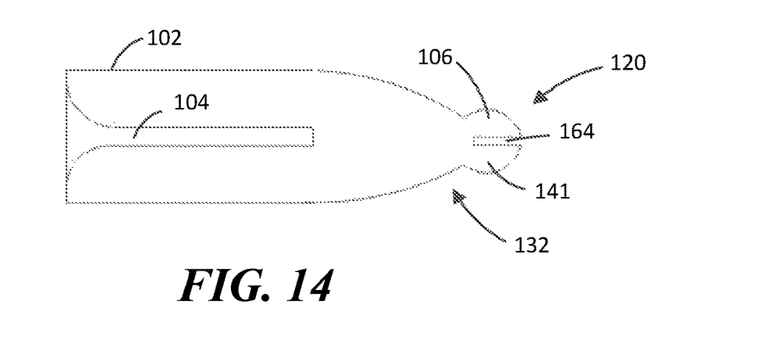
FIG. 14 depicts a bottom view of the foramen guide of FIG. 11.

As illustrated in the embodiments of FIGS. 2 and 3, the top surface of the elongated shaft 30 includes a tab 40 which extends from the approximate midpoint of shaft 30 to head 32. In one embodiment, the tab 40 gradually widens as it approaches head 32. The tab 40 may have additional shapes or sizes in other embodiments. The tab 40 extends to a protrusion 41 (see also FIG. 8) extending past the bottom surface of the shaft 30 to the end of the shaft 30 positioned opposite of the base 22. In one embodiment, protrusion 41 has a rounded shape; however other shapes are possible in other embodiments. Regardless of its shape, protrusion 41 exhibits a smooth surface so that it may easily move across the gums of a patient without causing injury or discomfort. In the embodiment illustrated in FIG. 6, protrusion 41 is hollow, forming a bowl 42 on the back side of shaft 30. In one embodiment illustrated in FIG. 10, the bowl 42 gradually tapers in a funnel shape to a hole 44 at its base. Hole 44 is shaped such that a needle 50 of a syringe 52 may cleanly pass through the head 32 and pierce the skin of a patient, as will be described in more detail below (FIG. 9).

Figure 6:
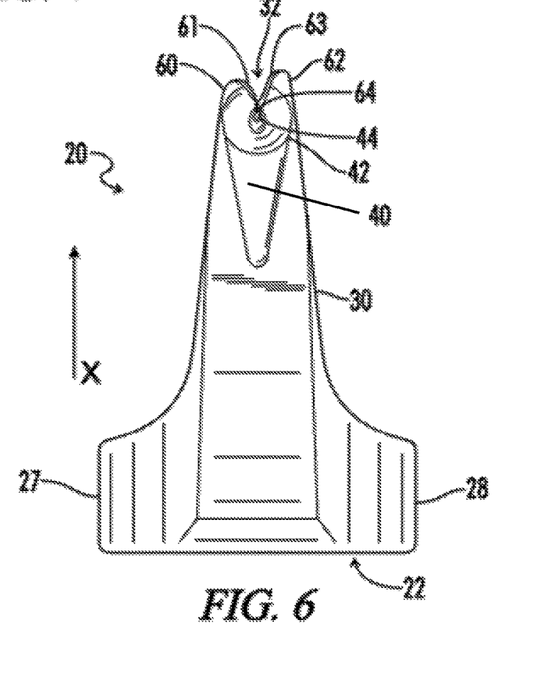
FIG. 6 depicts an additional bottom view of the foramen guide of FIG. 2.
Figure 7:
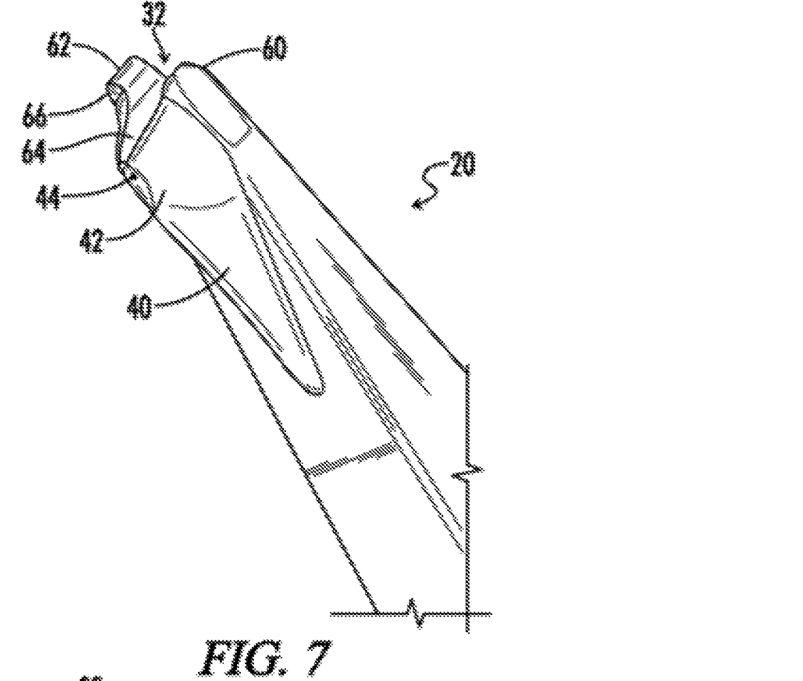
FIG. 7 depicts a bottom view of the shaft of the foramen guide of FIG. 2.

As illustrated in FIGS. 2 and 6, the head 32 further includes two adjacent rounded tabs 60 and 62 with inner walls 61 and 63, respectively. Tabs 60 and 62 are separated by a channel 64. The channel 64 extends slightly downward into bowl 42 to the hole 44. As embodied in FIGS. 2 and 6, one of the tabs (i.e., tab 62) is longer than the second tab (i.e., tab 60) at the end extending in the X direction, parallel to shaft 30. The exact length of adjacent tabs 60 and 62 may vary depending on the specific application of the guide 20. Turning to FIG. 3, tab 62 forms a curve 66 at its end which bends slightly outward and away from head 32.

In use, the user places the tongs 27 and 28 of the guide 20 around his finger 24 (FIG. 5). The elastic nature of the base 22 allows the tongs 27 and 28 to fit snugly around the user's finger 24, preventing the guide 20 from becoming displaced. In an alternate embodiment, the user secures a fastener placed at the base 22 (not shown) around his finger. The user then contacts the shaft 30 with his finger, applying pressure so that the protrusion 41 of head 32 is pressed against the patient's hard palate gum during movement. The rounded surface of the protrusion 41 allows the head 32 to easily slide across the gums while preventing injury or discomfort to the patient. Turning again to FIG. 7, the finger 24 contacts the guide 20 at the approximate midpoint of the shaft 30. The user slides the guide 20 across the gums of the patient searching for the posterior palatal foramen 10 (FIG. 9). The pressure applied by the user's finger 24 insures that the head 32 maintains constant contact with and presses against the hard palate gums. When the protrusion 41 of head 32 reaches the posterior palatal foramen 10, the head 18 is forced into the depression of the hard palate gum at the posterior palatal foramen 10. The movement of the protrusion 41 into the depression of the posterior palatal foramen 10 causes a change in the pressure along shaft 30. The user is able to sense this change in the pressure along shaft 30. This tactile sensation notifies the user that the posterior palatal foramen 10 has been reached. The protrusion 41 of head 32 is now located at and pressed against the hard palate gum depression of the posterior palatal foramen 10, much like a ball-and-socket arrangement. Note that, in other embodiments of guide 20 that do not have a bend in the shaft 30 (e.g., when the shaft 30 is straight), the user should still feel change in pressure caused by the movement of the protrusion 41 of head 32 into the depression of the posterior palatal foramen 10.

As illustrated in FIGS. 2, 3 and 6 and discussed previously, the head 32 includes two differently sized tabs 60 and 62, providing a channel 64 between the two tabs 60 and 62. The curved portion 66 of the longer wall 62 curves slightly outward away from head 32. In the embodiment illustrated in FIGS. 2, 3 and 6, the channel 64 extends slightly downward to convex bowl 42 and protrusion 41 until it reaches hole 44. The protrusion 41 form a convex-shaped probe that contacts patient's hard palate gum during use. In one exemplary embodiment, the protrusion 41 has a circumference of approximately two millimeters (mm). Other sizes of protrusion 41 are contemplated in other embodiments, depending on the intended application and use of guide 20. In other embodiments, the tabs 60 and 62 and protrusion 41 may have other types of shapes and dimensions. Note that the portions of the protrusion 41 contacting the patient's hard palate gums are preferably rounded, helping to prevent discomfort to the patient as the head 32 is slid across the patient's hard palate gum.

As illustrated in FIGS. 2, 3 and 9, the tabs 60 and 62 form a channel 64 which leads to the protrusion 41 and bowl 42. The funnel shaped bowl 42 extends downward to hole 44. In one embodiment, a user directs a needle 50 towards the curved portion 66 of the larger tab 62. The needle 50 then comes into contact with the curved portion 66 of the larger tab 62. The pressure exerted on the needle 50 causes it to maintain contact with and slide down tab 62, where it slides over walls 61 and 63 and is further guided through the channel 64. Continued application of pressure by the user's finger 24 moves the needle 50 through bowl 42 and into hole 44. The user may then apply additional pressure to the needle 50 so that it is inserted through this hole 44. In an alternate embodiment, the user may insert the needle directly into bowl 42 and hole 44 without coming into contact with tab 62 or curved portion 66. This embodiment may be utilized when the user is able to direct the needle 50 through hole 44 without the guidance of tab 62. In either embodiment, the head 32 guides the needle 50 to the posterior palatal foramen 10 when the head 32 is positioned in the depression of the posterior palatal foramen 10. Thus, once the posterior palatal foramen 10 has been located, as described above, the user can simply insert a needle 50 of a syringe through the hole 42 so that the needle 50 is guided to the proper location for administering anesthetic.

FIGS. 11-14 show another embodiment of the foramen guide 120. The foramen guide 120 includes a body 102 and a head 132 connected to the body 102. The body 102 can have a substantially cylindrical shape with an open interior area, i.e., hollow, to receive a finger of a user. The body 102 can have a length, i.e., the distance between an end and the head 132, such that some or all of the user's finger can be inserted into the body 102. The body 102 can also have a slot 104 starting at one end of the body 102 and extending towards the head 132 for some or all of the length of the body 102. The slot 104 provides some flexibility to the body 102 to permit the body 102 to accommodate fingers of different sizes and to permit some flexing of a finger when the device 120 is worn on the finger. In one embodiment, the body 102 and head 132 can be constructed from a rigid plastic material. However, in other embodiments, the body 102 and head 132 can be constructed from other materials, such as polymers, ceramics and metals.

The head 132 can have a protrusion 141 at an end that is located opposite the body 102. In one embodiment, the head 132 can taper, i.e., reduce in diameter, from the body 102 to the protrusion 141. In another embodiment, a portion of the head 132 can have an open interior, i.e., can be hollow, and can extend from the hollow portion of the body 102 to permit the user's finger to extend further into the guide 120 and to permit the tip of the user's finger be located in proximity to the protrusion 141. The protrusion 141 can have at least one rounded surface 106 to permit the protrusion 141 to slide along the patient's gums without causing injury or discomfort. In one embodiment, the protrusion 141 can have a substantially spherical shape formed from two substantially hemispherical tabs, but the protrusion can have different shapes, e.g., a hemispherical shape, in different embodiments.

The protrusion 141 can include a channel 164 that extends through the protrusion 141. The channel 164 can be shaped to receive a needle 50 of a syringe 52 and permit the needle 50 to pass through the protrusion 141 to access (and pierce) the skin of the patient. In one embodiment, the channel 164 can be open to permit access to the channel 164 either from the top of the protrusion 141 or an end of the protrusion 141. The protrusion 141 with the open channel 164 can include two tabs that are on either side of the channel 164. The tabs can form side walls for the channel 164 and can be used to direct the needle 50 to the posterior palatal foramen 10. In another embodiment, the channel 164 can be closed to form a hole through the protrusion 141 that can be accessed at the top of the protrusion.

In addition, the head 132 can also include a positioning channel 108 with side walls 110. In one embodiment, the positioning channel 108 can be formed from an outer surface of the head 132 and the side walls 110 can extend outwardly from the outer surface of the head 132. In another embodiment, the positioning channel 108 and some or all of the side walls 110 can be formed within the head 132. The positioning channel 108 can be connected to the channel 164 and can be used to direct the needle 50 to the channel 164 and then the posterior palatal foramen 10. In one embodiment, the side walls 110 can be positioned in a "V" shape in order to reduce the width of the positioning channel 108, similar to a funnel, as the positioning channel 108 approaches the protrusion 141 and the channel 164.

To use the guide 120, the user inserts his/her finger into the body 102 (and possibly the head 132) of the guide 120. The flexibility of the base 102 provided by the slot 104, permits the base 102 to fit snugly around the user's finger, preventing the guide 120 from becoming displaced. The user then applies pressure to the body 102 and/or head 132 with his/her finger, so that the protrusion 141 of head 132 is pressed against the patient's hard palate gum during movement. The rounded surface 106 of the protrusion 141 allows the head 132 to easily slide across the guns while preventing injury or discomfort to the patient. The user slides the guide 120 across the gums of the patient searching for the posterior palatal foramen 10. The pressure applied by the user's finger can insure that the head 132 and protrusion 141 maintain constant contact with and press against the hard palate gums. When the protrusion 141 of head 132 reaches the posterior palatal foramen 10, the protrusion 141 is forced into the depression of the hard palate gum at the posterior palatal foramen 10. The movement of the protrusion 141 into the depression of the posterior palatal foramen 10 causes a change in the pressure along body 102 and head 132. The user is able to sense this change in the pressure along body 102 and head 132. This tactile sensation notifies the user that the posterior palatal foramen 10 has been reached. The protrusion 141 of head 132 is now located at, and pressed against, the hard palate gum depression of the posterior palatal foramen 10, much like a ball-and-socket arrangement. The protrusion 141 can form a convex-shaped probe that contacts patient's hard palate gum during use. In one embodiment, the protrusion 141 has a circumference of approximately two millimeters (mm). Other sizes of protrusion 141 are contemplated in other embodiments, depending on the intended application and use of guide 120.

Once the posterior palatal foramen 10 has been located with the protrusion 141, the user can maintain pressure on the posterior palatal foramen 10 with the protrusion 141 while directing a needle 50 towards the positioning channel 108. The user can use the positioning channel 108 to direct the needle 50 to the channel 164. In another embodiment, the needle 50 can travel around one of the tabs of the protrusion 141 to reach the open end of the channel 164. After reaching the channel 164, the needle 50 can then travel down through channel 164 to the posterior palatal foramen 10 for injection into the patient.

In other words, the head 132 can guide the needle 50 to the posterior palatal foramen 10 when the protrusion 141 is positioned in the depression of the posterior palatal foramen 10. Thus, once the posterior palatal foramen 10 has been located, as described above, the user can simply insert a needle 50 of a syringe through the channel 164 so that the needle 50 is guided to the proper location for administering anesthetic.

In an additional embodiment, the guide 20, 120 of the present disclosure may be utilized to reduce or eliminate the pain from injections during dental procedures. The local application of pressure from the head 32 of the guide 20, 120 at the injection site may block pain fiber transmissions. Depression of the head 32 is sufficient to stimulate the pressure sensory nerves near the injection site. This influx of nerve impulses then inhibits the transmission of pain nerve impulses emanating from the injection site area.

In other embodiments, the guide 20, 120 is not limited to use in dental procedures but may also be utilized on other parts of the body. In one embodiment, the protrusion 41, 141 located on the head 32, 132 of the guide 20, 120 may be shaped to detect other anatomical changes or depressions on the body in addition to the depression of the posterior palatal foramen 10. In one example, the guide 20, 120 may be used to locate other injection sites, for instance the presence of veins on the arm.

The guide of the present disclosure provides for the quick and simple location of the posterior palatal foramen. The smooth shape of the protrusion allows the user to detect a change in pressure as the guide is moved along the hard palate and falls into the depression of the foramen, thus accurately identifying its location. The elastic nature of the base of the guide allows the base to contract inward and secure the apparatus to the user's finger. The location of the foramen and the application of pressure may be accomplished with a single hand, thus leaving the user's second hand to position and manipulate the needle and inject the anesthetic. The curved wall and tapered channel provide an efficient means to guide the needle to the location of the foramen and inject the anesthetic at this spot. Additionally, the guide applies pressure to the nerves within the foramen, thus reducing or eliminating the pain associated with the injection of anesthetic.

In additional embodiments, the guide may be utilized to locate an injection site on other parts of the body and lessen or prevent injection site pain by allowing the user to detect a change in pressure associated with a change in anatomy. In one example, directing the guide across the arm of a patient may detect the presence of a vein. Alternatively, the design of the base provides sufficient strength and stability to allow it to be utilized with other types of dental instruments for use in the oral cavity. As a result, the guide is not limited to the act of locating the posterior palatal foramen. Instead, the guide may include differently configured heads for use in a number of dental procedures. Such non-limiting examples of these instruments include mirrors, probes, picks or spatulas. As an example, a dental instrument may have a base at one end secured to a finger, as described above, and a mirror or other instrument instead of head 32 at the other end. The presently described guide may be used with a host of specialized equipment and employed in a number of different dental procedures.

It should be emphasized that the embodiments described herein are exemplary. Various changes and modifications to the embodiments would be apparent to a person of ordinary skill upon reading this disclosure.

Now, therefore, the following is claimed:

1. A method of injecting an anesthetic into a patient, comprising the steps of:
   securing a guide to a finger of a user such that a tip of the finger is located inside the guide and protected from a needle of a syringe;
   sliding, by the user, the guide across a hard palate gum of the patient such that a protrusion located at an end of a head of the guide is inserted into an area associated with a depression of a posterior palatal foramen, the protrusion comprising a first substantially hemispherical tab and a second substantially hemispherical tab separated from the first hemispherical tab by a channel;
   pressing the head of the guide against the hard palate gum with pressure applied to the guide by the finger of the user during the sliding to move the protrusion into the area associated with the depression;
   guiding the needle of the syringe to the area associated with the depression of the posterior palatal foramen via a positioning channel in the head defined by a first side wall connected to the first hemispherical tab and a second side wall connected to the second hemispherical tab and then to the channel in the protrusion inserted into the area associated with the depression; and
   applying the anesthetic to the area associated with the depression of the posterior palatal foramen via the needle.

2. The method of claim 1, wherein the applying the anesthetic includes maintaining pressure on the area associated with the depression with the protrusion during the application of the anesthetic.

3. The method of claim 1, wherein the positioning channel has a tapered surface, and wherein the guiding comprises sliding the needle across the tapered surface of the positioning channel to the channel.

4. The method of claim 1, wherein the guiding comprises detecting, by the user, a change in pressure on the guide, wherein the change in pressure corresponds to a movement of the protrusion into the depression.

5. The method of claim 1, wherein the first hemispherical tab has a curved portion, and wherein the guiding comprises sliding the needle across the curved portion to the channel.

6. The method of claim 1, wherein the first side wall and the second side wall are positioned such that a width of the positioning channel decreases as the positioning channel approaches the channel.

7. The method of claim 1, wherein the guide has a hollow cylindrical body connected to the head, and wherein the securing the guide to the finger comprises inserting the finger of the user into the hollow cylindrical body.

8. The method of claim 7, wherein the head has a hollow portion, and the securing the guide to the finger comprises inserting the tip of the finger into the hollow portion of the head.

9. The method of claim 1, wherein the applying the anesthetic includes maintaining pressure on the posterior palatal foramen with at least a portion of the head during the application of the anesthetic.

10. A dental instrument, comprising:
    a body for securing the dental instrument to a finger of a user, wherein the body is hollow and configured to receive the finger of the user such that a tip of the finger is located inside the body and protected from a needle of a syringe;
    a head connected to the body; and
    the head having a positioning channel defined by a first side wall and a second side wall and a protrusion located at an end of the head opposite the body, the protrusion having a first substantially hemispherical tab connected to the first side wall and a second substantially hemispherical tab connected to the second side wall and separated from the first hemispherical tab by a channel, the positioning channel and the channel provide a path to guide the needle of the syringe to and through the protrusion to a location to which an anesthetic is to be applied.

11. The dental instrument of claim 10, wherein the body has a substantially cylindrical shape.

12. The dental instrument of claim 10, wherein the first side wall and the second side wall are positioned such that a width of the positioning channel decreases as the positioning channel approaches the channel.

13. The dental instrument of claim 10, wherein the protrusion has a substantially spherical shape.

14. The dental instrument of claim 10, wherein the head has a hollow portion configured to receive the tip of the finger from the body such that the finger of the user is able to apply pressure to the head to insert the protrusion into a depression of a posterior palatal foramen as the dental instrument slides against a hard palate gum of a patient.

15. The dental instrument of claim 10, wherein the body comprises a slot extending from one end of the body to the head.

16. A method of injecting an anesthetic in a patient, comprising:
    securing a dental instrument to a finger of a user, the dental instrument comprising:
    a body to receive the finger of the user, wherein the body has a hollow portion configured to receive the finger of the user such that a tip of the finger is located inside the dental instrument and protected from a needle of a syringe; and
    a head extending from the body, the head having a positioning channel defined by a first side wall and a second side wall and a protrusion extending from an end of the head opposite the body, the protrusion comprising a first substantially hemispherical tab connected to the first side wall and a second substantially hemispherical tab connected to the second side wall and separated from the first hemispherical tab by a channel;

wherein the securing the dental instrument includes inserting the finger of the user into the hollow portion of the body;

applying pressure to the body of the dental instrument with the finger located inside the dental instrument;

sliding the dental instrument across hard palate gums of a patient while applying pressure to the body of the dental instrument;

inserting the protrusion into an area associated with a depression of the hard palate gums with the pressure applied to the body during the sliding of the dental instrument;

guiding a needle of a syringe to the area associated with the depression via the positioning channel and then the channel while the protrusion is inserted into the area associated with the depression; and applying the anesthetic to the area associated with the depression.

17. The method of claim 16, wherein the first side wall and the second side wall are positioned such that a width of the positioning channel decreases as the positioning channel approaches the channel.

18. The method of claim 16, wherein the applying the anesthetic includes maintaining pressure on the area associated with the depression with the protrusion during the application of the anesthetic.

19. The method of claim 16, wherein the head has a hollow portion continuous with the hollow portion of the body, and the securing the dental instrument includes inserting the finger of the user into the hollow portion of the head.

20. The method of claim 16, wherein the inserting comprises detecting, by the user, a change in pressure on the body, wherein the change in pressure corresponds to a movement of the protrusion into the depression.

* * * * *